United States Patent [19]

Kast et al.

[11] Patent Number: 5,389,602
[45] Date of Patent: Feb. 14, 1995

[54] HERBICIDAL TETRAHYDROPYRAN-2,4-DIONES

[75] Inventors: Juergen Kast, Boehl-Iggelheim; Dieter Kolassa, Ludwigshafen; Norbert Meyer, Ladenburg; Bruno Wuerzer, Otterstadt; Karl-Otto Westphalen, Speyer; Wilhelm Rademacher; Johann Jung, both of Limburgerhof, all of Germany

[73] Assignee: BASF Aktiengesellschaft, Ludwigshafen, Germany

[21] Appl. No.: 76,687

[22] Filed: Jun. 15, 1993

Related U.S. Application Data

[63] Continuation of Ser. No. 850,208, Mar. 12, 1992, abandoned, which is a continuation of Ser. No. 572,360, Aug. 27, 1990, abandoned, which is a continuation of Ser. No. 362,663, Jun. 7, 1989, abandoned.

[30] Foreign Application Priority Data

Jun. 7, 1988 [DE] Germany ............... 3819347

[51] Int. Cl.⁶ ............... C07D 413/04; A01N 43/74
[52] U.S. Cl. ............... 504/271; 504/266; 504/269; 504/275; 504/280; 504/283; 504/289; 504/292; 548/194; 548/204; 548/214; 548/247; 548/311.4; 548/365.7; 548/518; 549/60; 549/292
[58] Field of Search ............... 548/194, 204, 214, 247, 548/311.4, 365.7, 518; 549/60, 292; 504/266, 269, 271, 275, 280, 283, 289, 292

[56] References Cited

U.S. PATENT DOCUMENTS

| | | | |
|---|---|---|---|
| 4,008,067 | 2/1977 | Hirono et al. | 504/271 |
| 4,347,372 | 8/1982 | Fory et al. | 504/271 |
| 4,482,727 | 11/1984 | Lee | 549/291 |
| 4,666,510 | 5/1987 | Watson | 71/103 |
| 4,715,884 | 12/1987 | Watson | 71/90 |
| 4,842,638 | 6/1989 | Kart | 71/88 |

FOREIGN PATENT DOCUMENTS

| | | | |
|---|---|---|---|
| 2140803 | 12/1984 | United Kingdom | 71/90 |
| 8800945 | 2/1988 | WIPO | 549/265 |
| 8804652 | 6/1988 | WIPO | |

Primary Examiner—Robert Gerstl
Attorney, Agent, or Firm—Oblon, Spivak, McClelland, Maier, & Neustadt

[57] ABSTRACT

Tetrahydropyran-2,4-diones of the formula

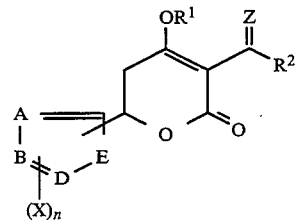

where $R^1$ is hydrogen; $C_1$-$C_6$-alkyl; $C_2$-$C_6$-alkenyl; $C_2$-$C_6$-alkynyl; substituted or unsubstituted phenyl; $C_1$-$C_6$-alkylsulfonyl; substituted or unsubstituted benzenesulfonyl; $C_3$-$C_6$-alkenylcarbonyl; or substituted or unsubstituted benzoyl;

$R^2$ is $C_1$-$C_6$-alkyl; $C_2$-$C_6$-alkenyl; $C_2$-$C_6$-alkynyl; $C_1$-$C_6$-haloalkyl; or $C_3$-$C_6$-cycloalkyl;

A, B and D are each =CH— or =N—;

E is oxygen, sulfur or —$NR^7$—.

$R^7$ is hydrogen; $C_1$-$C_6$-alkyl; $C_2$-$C_6$-alkenyl; $C_2$-$C_6$-alkanoyl; substituted or unsubstituted benzoyl; benzyl; or substituted or unsubstituted phenyl;

X is halogen; $C_1$-$C_6$-alkyl; substituted or unsubstituted $C_3$-$C_6$-cycloalkyl; $C_2$-$C_6$-alkenyl; $C_2$-$C_6$-alkynyl; $C_1$-$C_6$-alkoxy; $C_2$-$C_6$-alkenyloxy; $C_1$-$C_6$-alkylthio; $C_1$-$C_6$-alkoxycarbonyl; $C_2$-$C_6$-alkanoyloxy; substituted or unsubstituted benzyloxy; substituted or unsubstituted $NR^5R^6$; formyl; $C_2$-$C_6$-alkanoyl or its imine, oxime or Schiff's base; or substituted or unsubstituted phenyl;

n is 0, 1 or 2;

$R^3$, $R^4$, $R^5$ and $R^6$ are each hydrogen, $C_1$-$C_6$-alkyl, phenyl, $C_2$-$C_6$-alkanoyl, benzoyl and/or benzyl;

Z is oxygen or —$NOR^8$; and $R^8$ is substituted or unsubstituted $C_1$-$C_6$-alkyl; $C_2$-$C_6$-alkenyl; $C_2$-$C_6$-alkynyl; $C_2$-$C_6$-haloalkynyl; or substituted or unsubstituted thenyl;

their environmentally compatible salts, and agents containing them.

11 Claims, No Drawings

HERBICIDAL TETRAHYDROPYRAN-2,4-DIONES

This application is a continuation of application Ser. No. 07/850,208, filed on Mar. 12, 1992, now abandoned, which is a continuation of Ser. No. 07/572,360, filed on Aug. 27, 1990, now abandoned, which is a continuation of Ser. No. 07/362,663, filed on Jun. 7, 1989, now abandoned.

The present invention relates to tetrahydropyran-2,4-diones of the formula I

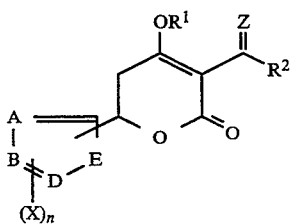

where
$R^1$ is hydrogen; $C_1$-$C_6$-alkyl which may be substituted by $C_1$-$C_6$-alkoxy or $C_1$-$C_6$-alkylthio; $C_2$-$C_6$-alkenyl; $C_2$-$C_6$-alkynyl; phenyl which may be monosubstituted to trisubstituted by halogen, nitro, cyano, $C_1$-$C_6$-alkyl, $C_1$-$C_6$-haloalkyl, $C_1$-$C_6$-alkoxy and/or $C_1$-$C_6$-alkylthio; $C_1$-$C_6$-alkylsulfonyl; benzenesulfonyl which may be monosubstituted to trisubstituted in the benzene ring by halogen, nitro, cyano, $C_1$-$C_6$-alkyl, $C_1$-$C_6$-haloalkyl, $C_1$-$C_6$-alkoxy and/or $C_1$-$C_6$-alkylthio; $C_2$-$C_6$-alkylcarbonyl; $C_3$-$C_6$-alkenylcarbonyl; or benzoyl which may be monosubstituted to trisubstituted in the benzene ring by halogen, cyano, nitro, $C_1$-$C_6$-alkyl, $C_1$-$C_6$-haloalkyl, $C_1$-$C_6$-alkoxy or $C_1$-$C_6$-alkylthio;

$R^2$ is $C_1$-$C_6$-alkyl, $C_2$-$C_6$-alkenyl, $C_2$-$C_6$-alkynyl, $C_1$-$C_6$-haloalkyl haloalkyl or $C_3$-$C_6$-cycloalkyl;

A, B and D are each $=$CH— or $=$N—;

E is oxygen, sulfur or —$NR^7$—;

$R^7$ is hydrogen; $C_1$-$C_6$-alkyl; $C_2$-$C_6$-alkenyl; $C_2$-$C_6$-alkanoyl; benzoyl which may be monosubstituted to trisubstituted in the benzene ring by $C_1$-$C_6$-alkyl, $C_1$-$C_6$-alkoxy, $C_1$-$C_6$-alkylthio, halogen, cyano, nitro and/or $C_1$-$C_6$-haloalkyl; benzyl; or phenyl which may be monosubstituted to trisubstituted by halogen, nitro, cyano, $C_1$-$C_6$-alkyl, $C_1$-$C_6$-haloalkyl, $C_1$-$C_6$-alkoxy and/or $C_1$-$C_6$-alkylthio;

X is halogen; $C_1$-$C_6$-alkyl; $C_1$-$C_6$-cycloalkyl which may be monosubstituted to trisubstituted by halogen, $C_1$-$C_6$-alkoxy and/or $C_1$-$C_6$-alkylthio; $C_2$-$C_6$-alkenyl; $C_2$-$C_6$-alkynyl; $C_1$-$C_6$-alkoxy; $C_2$-$C_6$-alkenyloxy; $C_1$-$C_6$-alkylthio; $C_1$-$C_6$-alkoxycarbonyl; $C_2$-$C_6$-alkanoyloxy; benzyloxy which may be monosubstituted to trisubstituted in the benzene ring by halogen, nitro, cyano, $C_1$-$C_6$-alkyl, $C_1$-$C_6$-alkoxy and/or $C_1$-$C_6$-haloalkyl; $NR^5R^6$; formyl or $C_2$-$C_6$-alkanoyl or its imine, oxime or Schiff's base; or phenyl which may be monosubstituted to trisubstituted by halogen, nitro, cyano, $C_1$-$C_6$-alkyl, $C_1$-$C_6$-alkoxy, $C_1$-$C_6$-haloalkyl and/or $NR_3R^4$;

n is 0, 1 or 2 and, where n is 2, the radicals X may be different;

$R^3$, $R^4$, $R^5$ and $R^6$ are each hydrogen, $C_1$-$C_6$-alkyl, phenyl, $C_2$-$C_6$-alkanoyl, benzoyl and/or benzyl;

Z is oxygen or an oxime ether radical —$NOR^8$; and $R^8$ is $C_1$-$C_6$-alkyl or $C_2$-$C_6$-alkenyl which may be monosubstituted to trisubstituted by halogen, $C_1$-$C_6$-alkoxy and/or $C_1$-$C_6$-alkylthio; $C_2$-$C_6$-alkynyl; $C_2$-$C_6$-haloalkynyl; $C_1$-$C_6$-alkyl or $C_2$-$C_6$-alkenyl, each of which may be monosubstituted to trisubstituted by phenyl, which may be monosubstituted to trisubstituted by halogen, nitro, cyano, $C_1$-$C_6$-alkyl, $C_1$-$C_6$-haloalkyl, $C_1$-$C_6$-alkoxy and/or $C_1$-$C_6$-alkylthio; or thenyl which may be monosubstituted to trisubstituted by halogen, and their environmentally compatible salts.

The present invention furthermore relates to the preparation of the compounds I, their use as herbicides and as growth regulators, and corresponding agents.

The compounds I may be in a plurality of tautomeric forms, all of which are embraced by the claim.

It is known that tetrahydropyran-2,4-dione oxime ether derivatives have a herbicidal action against monocotyledon plants. Examples of these are tetrahydropyran-2,4-diones which carry a phenyl radical in the 6-position (GB-A-21 40 803).

It is an object of the present invention to provide compounds which are better tolerated by crops (selectivity) and have a good action against weeds at lower application rates.

We have found that this object is achieved by the tetrahydropyran-2,4-dione derivatives defined at the outset.

We have also found that derivatives of the formula I in which Z is an oxime ether group (—$NOR^8$) have a good herbicidal action, and derivatives in which Z is oxygen have growth-regulating properties.

The tetrahydropyran-2,4-dione derivatives of the formula I where Z is $NOR^5$ can be obtained by reacting a tetrahydropyran-2,4-dione derivative of the formula I where Z is oxygen with a corresponding hydroxylamine or its ammonium compound $R^8ONH_2$ or $R^8ONH_3^\oplus W^\ominus$, respectively. $W^\ominus$ is an anion of an inorganic acid, such as chloride, bromide, iodide, bisulfate or phosphate; the reaction temperature is in general above 0° C. to about 80° C.

It is advantageous and preferable to react the tetrahydropyran-2,4-dione derivative I where Z is oxygen with the ammonium compound in the presence of a solid base in a solvent at from 20° to 80° C. Examples of suitable bases are carbonates, bicarbonates, acetates, alcoholates, hydroxides and oxides of alkali metals and alkaline earth metals, in particular sodium hydroxide, potassium hydroxide, magnesium oxide and calcium oxide. Organic bases, such as pyridine or tertiary amines, can also be used. The base is used in a stoichiometric amount or in excess.

Examples of suitable solvents are dimethyl sulfoxide, alcohols, such as methanol, ethanol or isopropanol, toluene, hexane, cyclohexane, chlorohydrocarbons, such as chloroform or dichloromethane, esters, such as ethyl acetate, and ethers, such as dioxane or tetrahydrofuran.

The tetrahydropyran-2,4-diones of the formula I where Z is oxygen are obtained in a conventional manner by reacting a corresponding tetrahydropyran-2,4-dione derivative of the formula II

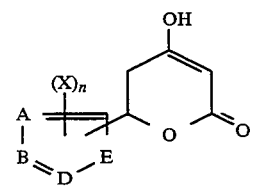

with an acyl chloride, by means of which the substituent $R^2$ is introduced, in the presence of a base (eg. triethylamine) in a diluent (eg. tetrahydrofuran), to give the enol ester, and then reacting the latter with an acidic or basic catalyst in the same solvent or in another solvent (eg. ethyl acetate or toluene) at from 0° to 100° C. Examples of acidic or basic catalysts are aluminum chloride, iron chloride, imidazole derivatives, eg. N-methylimidazole, and a pyridine, eg. dimethylaminopyridine.

There are several known processes for the preparation of the compounds of formula II, all of which start from an aldehyde:

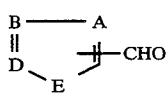

a) Reaction with a corresponding 4-bromo-3-methoxycrotonate in a solvent, such as ether, tetrahydrofuran or benzene, in the presence of zinc (J. Heterocycl. Chem. 21 (1984), 1755) or b) Reaction with a diketene in a solvent, such as dichloromethane, using a Lewis acid (eg. titanium tetrachloride) as a catalyst (Chem. Letters, 1975, 101) or c) Reaction with the dianion of an alkyl acetoacetate, for example with the disodium salt, in a solvent, such as tetrahydrofuran (Angew. Chem. 86 (1974), 40).

The aldehyde is obtained, for example, by oxidation of a corresponding alcohol, reduction of a carboxylic acid derivative or electrophilic aromatic substitution, for example a Vilsmeyer reaction.

The type of action of the novel tetrahydropyran-2,4-dione derivatives is influenced by the substitution pattern; for example, the compounds where Z is a radical N-OR$^8$ have a good herbicidal action, whereas the tetrahydropyran-2,4-dione derivatives where Z is oxygen preferentially have growth-regulating properties.

The compounds of the formula I where $R^1$ is hydrogen can occur in a plurality of tautomeric forms which formally differ from the formula I and are likewise embraced by the invention.

Where olefinically unsaturated substituents are present, E and Z isomers may occur in a known manner, these isomers also being embraced by the invention.

Where $R^8$ is haloalkyl or haloalkenyl, those having one, two or three halogen atoms are particularly preferred.

To provide a better overview, the compounds according to the invention are listed below in groups:

Furans, thiophenes and pyrroles of the formulae I.1 to I.6

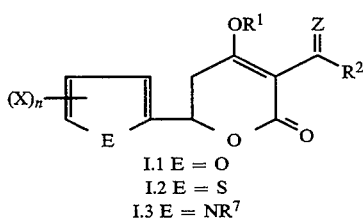

I.1 E = O
I.2 E = S
I.3 E = NR$^7$

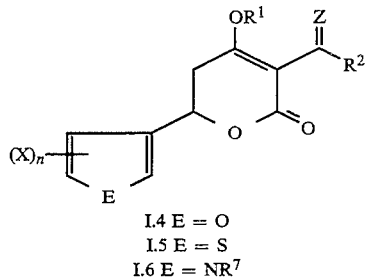

I.4 E = O
I.5 E = S
I.6 E = NR$^7$

Oxazoles, thiazoles and imidazoles of the formulae I.7 to I.15

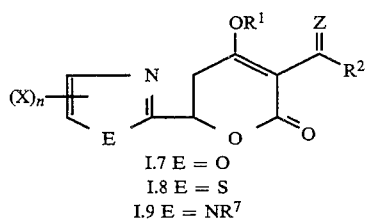

I.7 E = O
I.8 E = S
I.9 E = NR$^7$

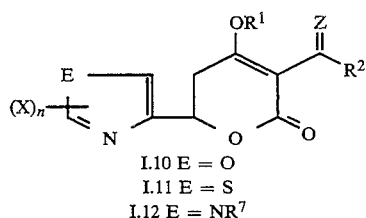

I.10 E = O
I.11 E = S
I.12 E = NR$^7$

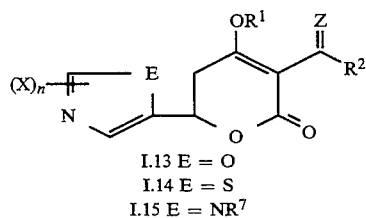

I.13 E = O
I.14 E = S
I.15 E = NR$^7$

Isoxazoles, isothiazoles and pyrazoles of the formulae I.16 to I.24

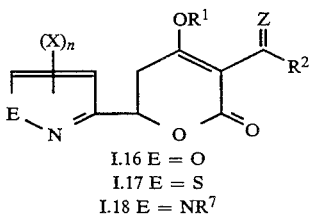

I.16 E = O
I.17 E = S
I.18 E = NR$^7$

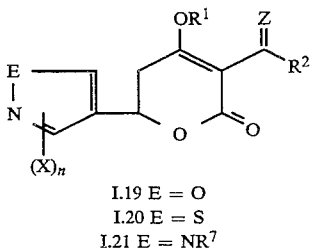

I.19 E = O
I.20 E = S
I.21 E = NR$^7$

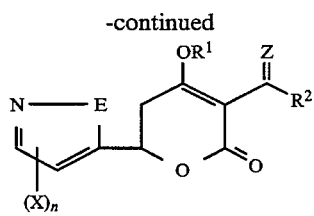

I.22 E = O
I.23 E = S
I.24 E = NR⁷

1,2,3-Oxadiazoles, 1,2,3-thiadiazoles and 1,2,3-triazoles of the formulae I.25 to I.30

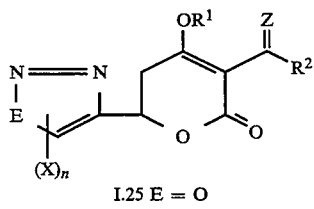

I.25 E = O
I.26 E = S
I.27 E = NR⁷

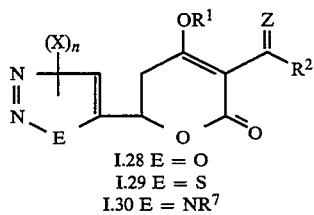

I.28 E = O
I.29 E = S
I.30 E = NR⁷

1,2,4-Oxadiazoles, 1,2,4-thiadiazoles and 1,2,4-triazoles of the formulae I.31 to I.36

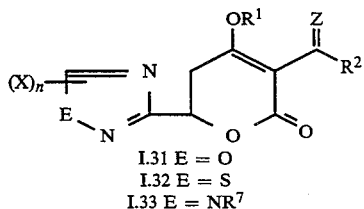

I.31 E = O
I.32 E = S
I.33 E = NR⁷

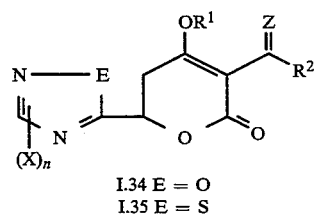

I.34 E = O
I.35 E = S
I.36 E = NR⁷

1,3,4-Oxadiazoles and 1,3,4-thiadiazoles of the formulae I.37 to I.39

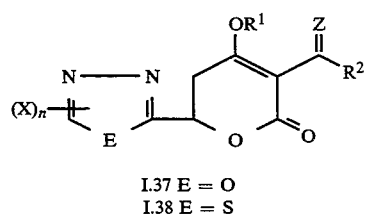

I.37 E = O
I.38 E = S

I.39 E = NR⁷

In formula I, $R^1$ is preferably hydrogen or an acid radical, such as $C_1$-$C_6$-alkylcarbonyl, $C_2$-$C_6$-alkenylcarbonyl, eg. acetyl, propionyl, acroyl, butyryl, isobutyryl, pivaloyl, valeroyl, unsubstituted or $C_1$-$C_6$-alkyl-substituted benzoyl, such as 4-methylbenzoyl, 4-ethylbenzoyl, 2,4,6-trimethylbenzoyl or benzoyl, p-methylphenylsulfonyl, or a monovalent metal cation, in particular sodium, potassium or one equivalent of a polyvalent cation, for example an alkaline earth metal cation, in particular magnesium or calcium, or other agriculturally usable cations, such as the manganese, copper, zinc or iron cation, or the ammonium, phosphonium, sulfonium or sulfoxonium cation, such as ammonium, tetraalkylammonium, benzyltrialkylammonium, trialkylsulfonium or trialkylsulfoxonium.

In formula I, $R^2$ is preferably a straight-chain, branched or cyclic alkyl radical of 1 to 6 carbon atoms, eg. methyl, ethyl, n-propyl, isopropyl, n-butyl, sec-butyl, isobutyl, tert-butyl, n-pentyl, isopentyl, sec-pentyl, tert-pentyl, neopentyl, n-hexyl, cyclopropyl, cyclobutyl, cyclopentyl or cyclohexyl.

Straight-chain alkyl radicals of 1 to 4 carbon atoms are particularly preferred, ie. methyl, ethyl, propyl or butyl, in particular ethyl or propyl.

Preferably, not more than three of the ring members A, B, D and E are simultaneously heteroatoms.

X is preferably fluorine, chlorine, bromine, methyl, ethyl, n-propyl, isopropyl, n-butyl, isobutyl, sec-butyl, tert-butyl, n-pentyl, cyclopropyl, cyclobutyl, cyclopentyl, cyclohexyl, methoxy, ethoxy, isopropoxy, tert-butoxy, methylthio, ethylthio, dimethylamino, diethylamino, dibutylamino, methoxymethyl, ethoxymethyl, methylthiomethyl, ethylthiomethyl, 1-methoxyethyl, 2-methoxythioethyl, 1,3-dimethoxypropyl, 2-ethoxyethyl, 1-methyl-2-methylthioethyl, 2-methyl-1-methylthiomethylpropyl, 1-methylbutyl, 2-methyl-1-propenyl, phenyl, 4-methylphenyl, 4-trifluoromethylphenyl, 2,4-dichlorophenyl, 4-methoxyphenyl, 2,4,6-trimethylphenyl, 3,5-dibromophenyl, 4-methylthiophenyl or 4-fluorophenyl, in particular methyl, ethyl, n-propyl, isopropyl, sec-butyl, tert-butyl, cyclopropyl, cyclopentyl, 1-methoxyethyl, dimethylamino, 4-fluorophenyl or chlorine.

$R^8$ is preferably methyl, ethyl, propyl, allyl, prop-2-ynyl, 3-fluoropropyl, trans-3-chloroprop-2-enyl, trans-but-2-enyl, cis-3-chloroprop-2-enyl, 2-chloroprop-2-enyl, but-2-ynyl, 2-methoxyethyl, E-4-(4-fluorophenyl)-but-2-enyl, E-4-(4-chlorophenyl)-but-2-enyl, E-4-(4-tertbutylphenyl)-but-2-enyl, E-4-(4-trifluorophenyl)-but-2-enyl, E-4-phenylbut-2-enyl, thenyl or 5-chlorothenyl, in particular methyl, ethyl, propyl, allyl, trans-3-chloroprop-2-enyl, trans-but-2-enyl or 5-chlorothenyl.

n is 0, 1 or 2.

$R^7$ is preferably methyl, ethyl, benzyl, phenyl, acetyl, benzoyl, isopropyl or 4-methoxyphenyl.

Preferred heterocycles in the 6-position of the tetrahydropyran-2,4-dione system of the formula I are furan-2-yl, thien-2-yl, pyrrol-2-yl, furan-3-yl, thien-3-yl, pyrrol-3-yl, isoxazol-5-yl, isoxazol-4-yl, isoxazol-3-yl, isothiazol-5-yl, isothiazol-4-yl, isothiazol-3-yl, pyrazol-5-yl, pyrazol-4-yl, pyrazol-3-yl, 1,3-oxazol-2-yl, 1,3-oxazol-4-yl, 1,3-oxazol-5-yl, 1,3-thiazol-2-yl, 1,3-thiazol-4-yl, 1,3-thiazol-5-yl, imidazol-2-yl, imidazol-4-yl, imidazol-5-yl, 1,2,3-oxadiazol-4-yl, 1,2,3-oxadiazol-5-yl, 1,2,3-thiadiazol-4-yl, 1,2,3-thiadiazol-5-yl, 1,2,3-triazol-4-yl, 1,2,3-triazol-5-yl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,2,4-triazol-5-yl, 1,3,4-oxadiazol-2-yl, 1,3,4-thiadiazol-2-yl and 1,3,4-triazol-2-yl. Furan-2-yl, thien-2-yl, pyrrol-2-yl, isoxazol-5-yl, isoxazol-3-yl, isothiazol-5-yl, 1,3-thiazol-4-yl, 1,3-thiazol-5-yl and imidazol-2-yl are particularly preferred and isoxazol-5-yl and isoxazol-3-yl are very particularly preferred.

Compounds I in which Z is an oxime ether group (—NOR⁸) are particularly suitable as herbicidal active ingredients. With respect to growth-regulating action, compounds I in which Z is oxygen are preferred. The novel tetrahydropyran-2,4-diones I, or the herbicidal agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, dispersions, wettable powders or water-dispersible granules by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutyl-naphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient. The active ingredients are employed in a purity of from 90 to 100, preferably from 95 to 100, % (according to the NMR spectrum).

The compounds I according to the invention may be formulated for instance as follows:

I. 90 parts by weight of compound no. 4.1 is mixed with 10 parts by weight of N-methyl-alpha-pyrrolidone. A mixture is obtained which is suitable for application in the form of very fine drops.

II. 20 parts by weight of compound no. 4.4 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 4.28 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 5.2 is dissolved in a mixture consisting of 25 parts by weight of cyclohexanone, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 5.4 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 6.3 is intimately mixed with 97 parts by weight of particulate kaolin. A dust is obtained containing 3% by weight of the active ingredient.

VII. 30 parts by weight of compound no. 1.1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 8.2 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The herbicidal or growth-regulating active ingredients may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The application rates for the herbicidal use of the active ingredients depend on the objective to be achieved, the time of the year, the plants to be combated and their growth stage, and are from 0.01 to 3.0, preferably 0.05 to 1.0, kg of active ingredient per hectare.

The tetrahydropyran-2,4-diones of the formula I in which Z is preferably oxygen may generally have a variety of influences on practically all plant development stages, and may therefore be used as growth regulators. The diversity of action of growth regulators depends especially on a) the type and variety of plant;

b) the time applied, with reference to the development stage of the plants and the time of the year;

c) the place and method of application (seed treatment, soil treatment, or application to foliage);

d) climatic factors, e.g., average temperature, amount of precipitate, sunshine and duration;

e) soil conditions (including fertilization);

f) the formulation of the active ingredient; and g) the concentration at which the active ingredient is applied.

A description of some of the various possibilities of using the growth regulators according to the invention in agriculture and horticulture is given below.

A. Vegetative plant growth can be inhibited to a considerable extent, a fact which is manifested particularly in a reduction in plant height. The treated plants thus have a compact habit; furthermore, the leaf color is darker.

Of advantage in practice is for example the reduction in grass growth on roadsides, canal embankments and on areas such as parks, sports-grounds, fruit orchards, lawns and airfields, thus reducing expensive and time-consuming mowing.

In fruit trees and other trees and bushes, cost-intensive pruning can be reduced.

A further feature of economic interest is the increase in the rigor of crops which tend to lodge, such as cereals, Indian corn, sunflowers and soybeans. The shortening and strengthening of the stem thus caused reduces or eliminates the danger of lodging under unfavorable weather conditions.

The use of growth regulators is also important for inhibiting plant height and changing the time of ripening in cotton. It is thus possible for this important crop to be harvested completely mechanically.

Growth regulators may also increase or inhibit lateral branching. This is of interest when, for instance in tobacco plants, it is desired to inhibit the formation of lateral shoots (suckers) in favor of leaf development.

With the growth-regulating compounds I, it is possible for instance in winter rape to considerably increase the resistance to freeze injury. On the one hand, upward growth and the development of a too luxuriant (and thus particularly frost-susceptible) leaf or plant mass are inhibited; on the other, the young rape plants are kept, in spite of favorable growth conditions, in the vegetative development stage before winter frosts begin. The danger of freeze injury is thus eliminated in plants which tend to lose prematurely their inhibition to bloom and pass into the generative phase. In other crops, too, e.g., winter cereals, it is advantageous if the plants are well tillered in the fall as a result of treatment with the compounds according to the invention, but enter winter with not too lush a growth. This is a preventive measure against increased susceptibility to freeze injury and—because of the relatively low leaf or plant mass—attack by various (especially fungus) diseases. The inhibition of vegetative growth also makes closer planting possible in numerous crops, which means an increase in yield, based on the area cropped.

B. Better yields both of plant parts and plant materials may be obtained with growth-regulating agents based on tetrahydropyran-2,4-diones I (Z=O). It is thus for instance possible to induce increased formation of buds, blossom, leaves, fruit, seed grains, roots and tubers, to increase the sugar content of sugarbeets, sugarcane and citrus fruit, to raise the protein content of cereals and soybeans, and to stimulate the increased formation of latex in rubber trees.

The tetrahydropyran-2,4-diones of the formula I (Z=O) may raise the yield by influencing plant metabolism or by promoting or inhibiting vegetative and/or generative plant growth.

C. It is also possible with growth regulators to shorten or lengthen growth stages and to accelerate or retard the ripening process in plant parts either before or after harvesting.

A factor of economic interest is for example the facilitation of harvesting made possible by a chemical, temporally concentrated loosening (abscission) of the adherence of stalks to the branches of citrus fruit, olive trees, and other kinds of pomes, drupes and indehiscent fruit. The same mechanism, i.e., promotion of the formation of separation layers between fruit or leaf and stem of the plant, is also essential for a readily controllable defoliation of crop plants, e.g., cotton.

D. Further, transpiration in crop plants may be reduced with growth regulators. This is particularly important for plants growing in agricultural areas which are expensive to irrigate, e.g., in arid or semi-arid areas. Irrigation frequency can be reduced by using the compounds according to the invention, making for lower costs. As a result of the use of growth regulators, the water available can be better utilized, because, inter alia, the size of the stomata opening is reduced;

a thicker epidermis and cuticle are formed;
penetration of the soil by the roots is improved;
the micro-climate in the stand is favorably influenced by the more compact growth.

The active ingredients to be used in accordance with the invention may be applied not only to the seed (as a disinfectant), but also to the soil, i.e., via the roots, and to the foliage by spraying.

As a result of the good crop plant tolerance, the application rate of the growth-regulating compounds in which Z is preferably oxygen may vary considerably. When seed is treated, active ingredient amounts of from 0.001 to 500, and preferably from 0.01 to 10, g per kg of seed are generally needed. When the soil or foliage is treated, rates of from 0.01 to 10, and preferably from 0.1 to 5, kg per hectare are generally considered to be sufficient.

In view of the number of application methods possible, the herbicidal and growth-regulating agents according to the invention, or agents containing them, may be used in a further large number of crops for removing unwanted plants. The following crops are given by way of example:

| Botanical name | Common name |
| --- | --- |
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beets, red beets |
| Brassica napus var. napus | rapeseed |
| Brassica napus var. napobrassica | swedes |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass |
| Daucus carota | carrots |
| Elais guineensis | oil palms |
| Fragaria vesca | strawberries |
| Glycine max | soybeans |
| Gossypium hirsutum (Gossypium arboreum, Gossypium herbaceum, Gossypium vitifolium) | cotton |
| Helianthus annuus | sunflowers |
| Helianthus tuberosus | Jerusalem artichoke |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicotiana tabacum (N. rustica) | tobacco |
| Olea europaea | olive trees |
| Oryza sativa | rice |
| Panicum miliaceum | millet |
| Phaseolus lunatus | limabeans |

-continued

| Botanical name | Common name |
| --- | --- |
| Phaseolus mungo | mungbeans |
| Phaseolus vulgaris | snapbeans, green beans, dry beans |
| Pennisetum glaucum | pearl millet |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | sorgo |
| Spinacia oleracea | spinach |
| Theobroma cacao | cacao plants |
| Trifolium pratense | red clover |
| Triticum aestivum | wheat |
| Triticum durum | durum wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the tetrahydropyran-2,4-diones I may be mixed and applied together with numerous representatives of other herbicidal or growth-regulating active ingredient groups. Examples of suitable components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, quinolinecarboxylic acid derivatives, aryloxy- or heteroaryloxy-phenylpropionic acids and salts, esters and amides thereof, etc.

It may also be useful to apply the compounds I, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

SYNTHESIS EXAMPLES

The directions given in the synthesis examples below may be used, after appropriate modifications of the starting materials, to obtain further compounds I. These compounds are given, with their physical data, in the table below. Compounds without these data are, in view of their structural similarity, expected to have a corresponding biological action. The radicals of the growth-regulating compounds I in which Z is oxygen correspond to those of the herbicidal compounds I listed in the table.

MANUFACTURING EXAMPLE a) 6-(3-isopropylisoxazol-5-yl)-tetrahydropyran-2,4-dione At −10° C., 61.5 g of methyl acetoacetate was dripped into 16.5 g of sodium hydride in 350 ml of THF. The mixture was cooled to −60° C. and 344 ml of 1.6 molar n-butyllithium solution in hexane was added. After all had been added, the mixture was stirred for 30 minutes at −60° C., and then 69.5 g of 5-formyl-3-isopropylisoxazole in 50 ml of THF was quickly dripped in at −60° C. The mixture was stirred for 30 minutes and then 10 ml of methanol followed by 30 g of acetic acid was added. After 10 minutes, the mixture was poured onto 500 g of ice, heated to room temperature, and stirred for 1 hour. The aqueous phase was extracted three times with methylene chloride, brought—with cooling—to a pH of 4.5 with dilute hydrochloric acid, and extracted with methylene chloride. The extract was washed with 5% strength sodium bicarbonate solution and water, dried with sodium sulfate, and the solvent was stripped off in a rotary evaporator. The residue was crystallized by stirring with methyl tert-butyl ether, followed by suction filtration. There was obtained 15 g of pure product.

b) 3-butyryl-6-(3-isopropylisoxazol-5-yl)-tetrahydropyran-2,4-dione 12.6 g of triethylamine was added to 27.9 g of 6-(3-isopropylisoxazol-5-yl)-tetrahydropyran-2,4-dione in 200 ml of THF. At 0° C., 13.3 g of butyryl chloride was dripped in and the mixture was stirred for one hour at 0° C. The mixture was evaporated, followed by partitioning between methylene chloride and water. The organic phase was worked up, i.e., extracted with water, 10% strength sodium carbonate solution and again with water, dried with sodium sulfate and evaporated again. The residue was dissolved in anhydrous methylene chloride and stirred for 48 hours with 1.3 g of 4-(N,N-dimethylamino)-pyridine. Removal of the solvent was followed by chromatography over silica gel with methylene chloride and methanol (98.5:1.5). The isolated compound was recrystallized from a small amount of cyclohexane. There was obtained 13 g of product.

c) 3-(1-ethoxyiminobutyl)-6-(3-isopropylisoxazol-5-yl)-tetrahydropyran-2,4-dione 3 g of 3-butyryl-6-(3-isopropylisoxazol-5-yl)-tetrahydropyran-2,4-dione was dissolved in 30 ml of anhydrous methanol. 0.9 g of sodium bicarbonate and then 1.1 g of ethoxyamine hydrochloride were added, and the mixture was stirred far 12 hours at room temperature and then evaporated to dryness. The residue was taken up in 50 ml of methylene chloride, washed once with water, twice with saturated sodium bicarbonate solution, and again with water, dried with sodium sulfate, and the solvent was stripped off. There was obtained 3.1 g of oxime ether.

TABLE 1

| No. | $R^1$ | $R^2$ | $R^8$ | Phys. data mp [°C.]; NMR [δ, ppm] |
|---|---|---|---|---|
| 1.1 | H | ethyl | ethyl | 1.19(t, 3H); 1.36(t, 3H); 2.29(s, 3H); 5.35(dd, 1H); 5.95(d, 1H) |
| 1.2 | H | ethyl | allyl | 1.19(t, 3H); 2.28(s, 3H); 4.54(d, 2H); 6.3(d, 1H) |
| 1.3 | H | ethyl | E-3-chloroprop-2-enyl | |
| 1.4 | H | ethyl | E-but-2-enyl | |
| 1.5 | H | ethyl | 5-chlorothien-2-ylmethyl | |
| 1.6 | H | propyl | ethyl | |
| 1.7 | H | propyl | allyl | |
| 1.8 | H | propyl | E-3-chloroprop-2-enyl | |
| 1.9 | H | propyl | E-but-2-enyl | |
| 1.10 | H | propyl | 5-chlorothien-2-ylmethyl | |

TABLE 2

| No. | $R^1$ | $R^2$ | $R^8$ | Phys. data mp [°C.]; NMR [δ, ppm] |
|---|---|---|---|---|
| 2.1 | H | ethyl | ethyl | |
| 2.2 | H | ethyl | allyl | |
| 2.3 | H | ethyl | E-3-chloroprop-2-enyl | |
| 2.4 | H | ethyl | E-but-2-enyl | |
| 2.5 | H | ethyl | 5-chlorothien-2-ylmethyl | |
| 2.6 | H | propyl | ethyl | 1.0(t, 3H); 1.36(t, 3H); 4.12(q, 2H); 5.39(dd, 1H); 7.32(s, 1H) |

TABLE 2-continued

[Structure: dichlorothiophene-substituted pyranone with OR¹, N-OR⁸, R² substituents]

| No. | R¹ | R² | R⁸ | Phys. data mp [°C.]; NMR [δ, ppm] |
|---|---|---|---|---|
| 2.7 | H | propyl | allyl | |
| 2.8 | H | propyl | E-3-chloroprop-2-yl | 1.0(t, 3H); 4.54(d, 2H); 5.4(dd, 1H); 6.0–6.2(m1, H); 6.4(d, 1H) |
| 2.9 | H | propyl | E-but-2-enyl | |
| 2.10 | H | propyl | 5-chlorothien-2-ylmethyl | |

TABLE 3

[Structure: N-(3-trifluoromethylphenyl)pyrrole-substituted pyranone with OR¹, N-OR⁸, R² substituents]

| No. | R¹ | R² | R⁸ | Phys. data mp [°C.]; NMR [δ, ppm] |
|---|---|---|---|---|
| 3.1 | H | ethyl | ethyl | 1.21(t, 3H); 1.35(t, 3H); 4.13(q, 2H); 4.57(dd, 1H); 6.4(m, 1H) |
| 3.2 | H | ethyl | allyl | 1.22(t, 3H); 4,55(d, 2H); 5.3–5.6(m, 3H); 5.9–6.1(m, 1H); 6.4(m, 1H) |
| 3.3 | H | ethyl | E-3-chloroprop-2-enyl | 1.17(t, 3H); 4.54(d, 2H); 5.47(dd, 1H); 6.12(dt, 1H); 6.3–6.5(m, 2H) |
| 3.4 | H | ethyl | E-but-2-enyl | 1.2(t, 3H); 1.8(d, 3H); 4.48(d, 2H); 5.46(dd, 1H); 5.47–5.8(m, 1H) |
| 3.5 | H | ethyl | 5-chlorothien-2-ylmethyl | |
| 3.6 | H | propyl | ethyl | |
| 3.7 | H | propyl | allyl | |
| 3.8 | H | propyl | E-3-chloroprop-2-enyl | |
| 3.9 | H | propyl | E-but-2-enyl | |
| 3.10 | H | propyl | 5-chlorothien-2-ylmethyl | |
| 3.11 | H | ethyl | 4-(4-fluorophenyl)-but-3-enyl | 1.21(t, 3H); 4.19(t, 2H); 5.44(m, 1H) |
| 3.12 | H | ethyl | 4-(4-methoxyphenyl)-but-2-enyl | 1.21(t, 3H; 2,78(dd, 1H); 3.39(d, 2H); 3.77(s, 3H); 4.5(d, 2H) |
| 3.13 | H | ethyl | 4-(4-fluorophenyl)-but-2-enyl | 1.2(t, 3H); 2.79(dd, 1H); 3.44(d, 2H); 4.52(d, 2H); 5.47(dd, 1H) |
| 3.14 | H | ethyl | propargyl | 1.19(t, 3H); 2,58(t, 1H); 4.68(d, 2H); 5.48(dd, 1H); 6.4(dd, 1H) |
| 3.15 | H | ethyl | cyclopent-2-enyl | 1.19(t, 3H); 5.2–5.35(m, 1H); 5.46(dd, 1H); 5.85–6.0(m, 1H) |

TABLE 4

[Structure: 3-isopropylisoxazol-5-yl substituted pyranone with OR¹, N-OR⁸, R² substituents]

| No. | R¹ | R² | R⁸ | Phys. data mp [°C.]; NMR [δ, ppm] |
|---|---|---|---|---|
| 4.1 | H | ethyl | ethyl | 1.21(t, 3H); 1.23(d, 6H); 1.38(t, 3H); 5.56(dd, 1H); |
| 4.2 | H | ethyl | allyl | 1.21(t, 3H); 1.3(d, 6H); 6.3(s, 1H); |
| 4.3 | H | ethyl | E-3-chloroprop-2-enyl | 1.19(t, 3H); 1.3(d, 6H); 5.58(dd, 1H); 6.45(d, 1H); |
| 4.4 | H | ethyl | E-but-2-enyl | 1.20(t, 3H); 1.29(d, 6H); 5.54(dd, 1H); 6.28(s, 1H); |
| 4.5 | H | ethyl | 5-chlorothien-2-ylmethyl | |
| 4.6 | H | ethyl | methyl | |
| 4.7 | H | ethyl | propyl | |

TABLE 4-continued i-C₃H₇ group on isoxazole, structure with OR¹, N-OR⁸, R² substituents on pyranone ring

| No. | R¹ | R² | R⁸ | Phys. data mp [°C.]; NMR [δ, ppm] |
|---|---|---|---|---|
| 4.8 | H | ethyl | prop-2-ynyl | |
| 4.9 | H | ethyl | 3-fluoropropyl | |
| 4.10 | H | ethyl | Z-3-chloroprop-2-enyl | |
| 4.11 | H | ethyl | 2-chloroprop-2-enyl | |
| 4.12 | H | ethyl | but-2-ynyl | |
| 4.13 | H | ethyl | 2-methoxyethyl | |
| 4.14 | H | ethyl | E-4(4-fluorophenyl)but-2-enyl | |
| 4.15 | H | ethyl | E-4(4-trifluorophenyl)but-2-enyl | |
| 4.16 | H | ethyl | E-4(4-chlorophenyl)but-2-enyl | |
| 4.17 | H | ethyl | E-4(4-t-butylphenyl)but-2-enyl | |
| 4.18 | H | ethyl | E-4-phenylbut-2-enyl | |
| 4.19 | H | ethyl | benzyl | |
| 4.20 | H | ethyl | 4-fluorobenzyl | |
| 4.21 | H | ethyl | 3-trifluoromethylbenzyl | |
| 4.22 | H | ethyl | 4-nitrobenzyl | |
| 4.23 | H | ethyl | 4-cyanobenzyl | |
| 4.24 | H | ethyl | 3-chlorobenzyl | |
| 4.25 | H | ethyl | thien-2-ylmethyl | |
| 4.26 | H | ethyl | 5-bromothien-2-ylmethyl | |
| 4.27 | H | propyl | ethyl | 0.99(t, 3H); 1.29(d, 6H); 1.35(3, tH); 5.52(dd, 1H); |
| 4.28 | H | propyl | allyl | 0.98(t, 3H); 1.27(d, 6H); 4.54(d, 2H); 6.27(s, 1H); |
| 4.29 | H | propyl | E-3-chloroprop-2-enyl | 0.96(t, 3H); 1.27(d, 6H); 4.54(d, 2H); 5.53(dd, 1H); |
| 4.30 | H | propyl | E-but-2-enyl | 0.98(t, 3H); 1.28(d, 6H); 1.8(d. 3H); 5.52(dd, 1H); |
| 4.31 | H | propyl | 5-chlorothien-2-ylmethyl | |
| 4.32 | H | propyl | methyl | |
| 4.33 | H | propyl | propyl | |
| 4.34 | H | propyl | prop-2-ynyl | |
| 4.35 | H | propyl | 3-fluoropropyl | |
| 4.36 | H | propyl | 2-3-chloroprop-2-enyl | |
| 4.37 | H | propyl | 2-chloroprop-2-enyl | |
| 4.38 | H | propyl | but-2-ynyl | |
| 4.39 | H | propyl | 2-methoxyethyl | |
| 4.40 | H | propyl | E-4(4-fluorophenyl)but-2-enyl | |
| 4.41 | H | propyl | E-4(4-chlorophenyl)but-2-enyl | |
| 4.42 | H | propyl | E-4(4-t-butylphenyl)but-2-enyl | |
| 4.43 | H | propyl | E-4(4-trifluoromethylphenyl-but-2-enyl | |
| 4.44 | H | propyl | E-4-phenylbut-2-enyl | |
| 4.45 | H | propyl | benzyl | |
| 4.46 | H | propyl | 4-fluorobenzyl | |
| 4.47 | H | propyl | 3-trifluoromethylbenzyl | |
| 4.48 | H | propyl | 4-nitrobenzyl | |
| 4.49 | H | propyl | 4-cyanobenzyl | |
| 4.50 | H | propyl | 3-chlorobenzyl | |
| 4.51 | H | propyl | thien-2-ylmethyl | |
| 4.52 | H | propyl | 5-bromothien-2-ylmethyl | |

TABLE 5

H₅C₂ group on isoxazole, structure with OR¹, N-OR⁸, R² substituents on pyranone ring

| No. | R¹ | R² | R⁸ | Phys. data mp [°C.]; NMR [δ, ppm] |
|---|---|---|---|---|
| 5.1 | H | ethyl | ethyl | |
| 5.2 | H | ethyl | allyl | 1.21(t, 3H); 1.29(t, 3H); 2.73(q, 2H); 4.58(d, 2H); 6.29(s, 1H); |
| 5.3 | H | ethyl | E-3-chloroprop-2-enyl | |
| 5.4 | H | ethyl | E-but-2-enyl | 1.19(t, 3H); 1.23(t, 3H); 1.81(d, 3H); 4.48(d, 2H); 6.28(s, 1H); |
| 5.5 | H | ethyl | 5-chlorothien-2-ylmethyl | |
| 5.6 | H | ethyl | methyl | |
| 5.7 | H | ethyl | propyl | |
| 5.8 | H | ethyl | prop-2-ynyl | |
| 5.9 | H | ethyl | 3-fluoropropyl | |

TABLE 5-continued

[Structure: Et-isoxazole fused pyranone with OR¹ and C(R²)=N-OR⁸ substituents]

| No. | R¹ | R² | R⁸ | Phys. data mp [°C.]; NMR [δ, ppm] |
|---|---|---|---|---|
| 5.10 | H | ethyl | 2-3-chloroprop-2-enyl | |
| 5.11 | H | ethyl | 2-chloroprop-2-enyl | |
| 5.12 | H | ethyl | but-2-ynyl | |
| 5.13 | H | ethyl | 2-methoxyethyl | |
| 5.14 | H | ethyl | E-4(4-t-butylphenyl)but-2-enyl | |
| 5.15 | H | ethyl | E-4(4-fluorophenyl)but-2-enyl | |
| 5.16 | H | ethyl | E-4(4-chlorophenyl)but-2-enyl | |
| 5.17 | H | ethyl | E-4(4-trifluoromethylphenyl)but-2-enyl | |
| 5.18 | H | ethyl | E-4-phenylbut-2-enyl | |
| 5.19 | H | ethyl | benzyl | |
| 5.20 | H | ethyl | 4-fluorobenzyl | |
| 5.21 | H | ethyl | 3-trifluoromethylbenzyl | |
| 5.22 | H | ethyl | 4-nitrobenzyl | |
| 5.23 | H | ethyl | 4-cyanobenzyl | |
| 5.24 | H | ethyl | 3-chlorobenzyl | |
| 5.25 | H | ethyl | thien-2-ylmethyl | |
| 5.26 | H | ethyl | 5-bromothien-2-ylmethyl | |
| 5.27 | H | propyl | ethyl | |
| 5.28 | H | propyl | allyl | |
| 5.29 | H | propyl | E-3-chloroprop-2-enyl | |
| 5.30 | H | propyl | E-but-2-enyl | |
| 5.31 | H | propyl | 5-chlorothien-2-ylmethyl | |
| 5.32 | H | propyl | methyl | |
| 5.33 | H | propyl | propyl | |
| 5.34 | H | propyl | prop-2-ynyl | |
| 5.35 | H | propyl | 3-fluoropropyl | |
| 5.36 | H | propyl | Z-3-chloroprop-2-enyl | |
| 5.37 | H | propyl | 2-chloroprop-2-enyl | |
| 5.38 | H | propyl | but-2-ynyl | |
| 5.39 | H | propyl | 2-methoxyethyl | |
| 5.40 | H | propyl | E-4(4-t-butylphenyl)but-2-enyl | |
| 5.41 | H | propyl | E-4(4-fluorophenyl)but-2-enyl | |
| 5.42 | H | propyl | E-4(4-chlorophenyl)but-2-enyl | |
| 5.43 | H | propyl | E-4(4-trifluoromethylphenyl)but-2-enyl | |
| 5.44 | H | propyl | E-4-phenylbut-2-enyl | |
| 5.45 | H | propyl | benzyl | |
| 5.46 | H | propyl | 4-fluorobenzyl | |
| 5.47 | H | propyl | 3-trifluoromethylbenzyl | |
| 5.48 | H | propyl | 4-nitrobenzyl | |
| 5.49 | H | propyl | 4-cyanobenzyl | |
| 5.50 | H | propyl | 3-chlorobenzyl | |
| 5.51 | H | propyl | thien-2-ylmethyl | |
| 5.52 | H | propyl | 5-bromothien-2-ylmethyl | |

TABLE 6

[Structure: s-Butyl-isoxazole fused pyranone with OR¹ and C(R²)=N-OR⁸ substituents]

| No. | R¹ | R² | R⁸ | Phys. data mp [°C.]; NMR [δ, ppm] |
|---|---|---|---|---|
| 6.1 | H | ethyl | ethyl | 0.88(t, 3H); 1.36(t, 3H); 4.12(q, 2H); 5.53(dd, 1H); 6.23(s, 1H) |
| 6.2 | H | ethyl | allyl | 0.89(t, 3H); 1.05(m, 6H); 4.55(d, 2H); 5.37-5.6(m, 3H); 6.26(s, 1H) |
| 6.3 | H | ethyl | E-3-chloroprop-2-enyl | 0.87(t, 3H); 1.16(t, 3H); 1.25(d, 3H); 4.55(d, 2H); 5.54(dd, 1H); 6.27(s, 1H) |
| 6.4 | H | ethyl | E-but-2-enyl | 0.86(t, 3H); 1.17(t, 3H); 1.26(d, 3H); 5.52(dd, 1H); 6.26(s, 1H) |
| 6.5 | H | ethyl | 5-chlorothien-2-ylmethyl | 0.88(t, 3H); 1.12(t, 3H); 1.25(d, 3H); 5.09(s, 2H); 5.5(dd, 1H) |
| 6.6 | H | ethyl | methyl | |
| 6.7 | H | ethyl | propyl | |
| 6.8 | H | ethyl | prop-2-ynyl | |
| 6.9 | H | ethyl | 3-fluoropropyl | |
| 6.10 | H | ethyl | Z-3-chloroprop-2-enyl | |
| 6.11 | H | ethyl | 2-chloroprop-2-enyl | |

TABLE 6-continued

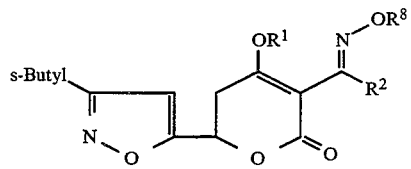

| No. | R¹ | R² | R⁸ | Phys. data mp [°C.]; NMR [δ, ppm] |
|---|---|---|---|---|
| 6.12 | H | ethyl | but-2-ynyl | |
| 6.13 | H | ethyl | E-4(4-t-butylphenyl)but-2-enyl | |
| 6.14 | H | ethyl | 2-methoxyethyl | |
| 6.15 | H | ethyl | E-4(4-fluorophenyl)but-2-enyl | |
| 6.16 | H | ethyl | E-4(4-chlorophenyl)but-2-enyl | |
| 6.17 | H | ethyl | E-4(4-trifluoromethylphenyl)but-2-enyl | |
| 6.18 | H | ethyl | E-4-phenylbut-2-enyl | |
| 6.19 | H | ethyl | benzyl | |
| 6.20 | H | ethyl | 4-fluorobenzyl | |
| 6.21 | H | ethyl | 3-trifluoromethylbenzyl | |
| 6.22 | H | ethyl | 4-nitrobenzyl | |
| 6.23 | H | ethyl | 4-cyanobenzyl | |
| 6.24 | H | ethyl | 3-chlorobenzyl | |
| 6.25 | H | ethyl | thien-2-ylmethyl | |
| 6.26 | H | ethyl | 5-bromothien-2-ylmethyl | |
| 6.27 | H | propyl | ethyl | 0.9(t, 3H); 1.0(t, 3H); 1.25(d, 3H); 1.37(t, 3H); 4.13(q, 2H); 5.54(dd, 1H) |
| 6.28 | H | propyl | allyl | 0.86(t, 3H); 0.95(t, 3H); 1.27(d, 3H); 4.54(d, 2H); 5.3–5.6(m, 3H); 6.28(s, 1H) |
| 6.29 | H | propyl | E-3-chloroprop-2-enyl | 0.89(t, 3H); 1.0(t, 3H); 1.25(d, 3H); 1.8(d, 3H); 4.46(d, 2H); 5.5(dd, 1H) |
| 6.30 | H | propyl | E-but-2-enyl | 0.9(t, 3H); 0.99(t, 3H); 1.26(d, 3H); 4,54(d, 2H); 5.54(dd, 1H) |
| 6.31 | H | propyl | 5-chlorothien-2-ylmethyl | 0.9(t, 3H); 0.99(t, 3H); 1.25(d, 3H); 5.1(s, 2H); 5.5(dd, 1H); 6.24(s, 1H) |
| 6.32 | H | propyl | methyl | |
| 6.33 | H | propyl | propyl | |
| 6.34 | H | propyl | prop-2-ynyl | 0.86(t, 3H); 0.95(t, 3H); 1.26(d, 3H); 2.59(t, 1H); 4.67(d, 2H); 5.53(dd, 1H) |
| 6.35 | H | propyl | 3-fluoropropyl | |
| 6.36 | H | propyl | Z-3-chloroprop-2-enyl | |
| 6.37 | H | propyl | 2-chloroprop-2-enyl | |
| 6.38 | H | propyl | but-2-ynyl | |
| 6.39 | H | propyl | 2-methoxyethyl | |
| 6.40 | H | propyl | E-4(4-t-butylphenyl)but-2-enyl | 0.89(t, 3H); 0.99(t, 3H); 1.26(d, 3H); 3.47(d, 2H); 4.52(d, 2H); 5.5(dd, 1H) |
| 6.41 | H | propyl | E-4(4fFluorophenyl)but-2-enyl | 0.86(t, 3H); 0.97(t, 3H); 1.27(d, 3H); 3.45(d, 2H); 4.5(d, 2H); 5.53(dd, 1H) |
| 6.42 | H | propyl | E-4(4-chlorophenyl)but-2-enyl | |
| 6.43 | H | propyl | E-4(4-trifluoromethylphenyl)but-2-enyl | |
| 6.44 | H | propyl | E-4-phenylbut-2-enyl | |
| 6.45 | H | propyl | benzyl | |
| 6.46 | H | propyl | 4-fluorobenzyl | |
| 6.47 | H | propyl | 3-trifluoromethylbenzyl | |
| 6.48 | H | propyl | 4-nitrobenzyl | |
| 6.49 | H | propyl | 4-cyanobenzyl | |
| 6.50 | H | propyl | 3-chlorobenzyl | |
| 6.51 | H | propyl | thien-2-ylmethyl | |
| 6.52 | H | propyl | 5-bromothien-2-ylmethyl | |
| 6.53 | H | propyl | 4-chlorobenzyl | 0.88(t, 3H); 0.94(t, 3H); 1.25(d, 3H); 5.0(s, 2H); 5.5(dd, 1H); 6.23(s, 1H); |

TABLE 7

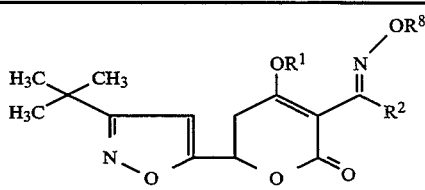

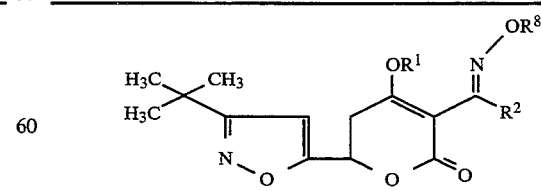

| No. | R¹ | R² | R⁸ | Phys. data mp [°C.]; NMR [δ, ppm] |
|---|---|---|---|---|
| 7.1 | H | ethyl | ethyl | |
| 7.2 | H | ethyl | allyl | |
| 7.3 | H | ethyl | E-3-chloroprop-2-enyl | |
| 7.4 | H | ethyl | E-but-2-enyl | |
| 7.5 | H | ethyl | 5-chlorothien-2-ylmethyl | |
| 7.6 | H | ethyl | methyl | |

TABLE 7-continued

| No. | R$^1$ | R$^2$ | R$^8$ | Phys. data mp [°C.]; NMR [δ, ppm] |
|---|---|---|---|---|
| 7.7 | H | ethyl | propyl | |
| 7.8 | H | ethyl | prop-2-ynyl | |
| 7.9 | H | ethyl | 3-fluoropropyl | |
| 7.10 | H | ethyl | Z-3-chloroprop-2-enyl | |
| 7.11 | H | ethyl | 2-chloroprop-2-enyl | |
| 7.12 | H | ethyl | but-2-ynyl | |
| 7.13 | H | ethyl | 2-methoxyethyl | |
| 7.14 | H | ethyl | E-4(4-t-butylphenyl)but-2-enyl | |
| 7.15 | H | ethyl | E-4(4-fluorophenyl)but-2-enyl | |
| 7.16 | H | ethyl | E-4(4-chlorophenyl)but-2-enyl | |
| 7.17 | H | ethyl | E-4(4-trifluoromethyl-phenyl)but-2-enyl | |
| 7.18 | H | ethyl | E-4-phenylbut-2-enyl | |
| 7.19 | H | ethyl | benzyl | |
| 7.20 | H | ethyl | 4-fluorobenzyl | |
| 7.21 | H | ethyl | 3-trifluoromethylbenzyl | |
| 7.22 | H | ethyl | 4-nitrobenzyl | |
| 7.23 | H | ethyl | 4-cyanobenzyl | |
| 7.24 | H | ethyl | 3-chlorobenzyl | |
| 7.25 | H | ethyl | thien-2-ylmethyl | |
| 7.26 | H | ethyl | 5-bromothien-2-ylmethyl | |
| 7.27 | H | propyl | ethyl | |
| 7.28 | H | propyl | allyl | |
| 7.29 | H | propyl | E-3-chloroprop-2-enyl | |
| 7.30 | H | propyl | E-but-2-enyl | |
| 7.31 | H | propyl | 5-chlorothien-2-ylmethyl | |
| 7.32 | H | propyl | methyl | |
| 7.33 | H | propyl | propyl | |
| 7.34 | H | propyl | prop-2-ynyl | |
| 7.35 | H | propyl | 3-fluoropropyl | |
| 7.36 | H | propyl | Z-3-chloroprop-2-enyl | |
| 7.37 | H | propyl | 2-chloroprop-2-enyl | |
| 7.38 | H | propyl | but-2-ynyl | |
| 7.39 | H | propyl | 2-methoxyethyl | |
| 7.40 | H | propyl | E-4(4-t-butylphenyl)but-2-enyl | |
| 7.41 | H | propyl | E-4(4-fluorophenyl)but-2-enyl | |
| 7.42 | H | propyl | E-4(4-chlorophenyl)but-2-enyl | |
| 7.43 | H | propyl | E-4(4-trifluoromethyl-phenyl)but-2-enyl | |
| 7.44 | H | propyl | E-4-phenylbut-2-enyl | |
| 7.45 | H | propyl | benzyl | |
| 7.46 | H | propyl | 4-fluorobenzyl | |
| 7.47 | H | propyl | 3-trifluoromethylbenzyl | |
| 7.48 | H | propyl | 4-nitrobenzyl | |
| 7.49 | H | propyl | 4-cyanobenzyl | |
| 7.50 | H | propyl | 3-chlorobenzyl | |
| 7.51 | H | propyl | thien-2-ylmethyl | |
| 7.52 | H | propyl | 5-bromothien-2-ylmethyl | |

TABLE 8

| No. | R$^1$ | R$^2$ | R$^8$ | Phys. data mp [°C.]; NMR [δ, ppm] |
|---|---|---|---|---|
| 8.1 | H | ethyl | ethyl | |
| 8.2 | H | ethyl | allyl | 1.19(t, 3H); 1.5–2.2 (m, 8H); 4.55(d, 2H); 6.24(s, 1H) |
| 8.3 | H | ethyl | E-3-Chloroprop-2-enyl | 1.12(t, 3H); 1.5–2.2 (m, 8H); 4.55(d, 2H); 5.54(dd, 1H) 6.26(s, 1H) |
| 8.4 | H | ethyl | E-but-2-enyl | |
| 8.5 | H | ethyl | 5-chlorothien-2-ylmethyl | |
| 8.6 | H | ethyl | methyl | |
| 8.7 | H | ethyl | propyl | |
| 8.8 | H | ethyl | prop-2-ynyl | |
| 8.9 | H | ethyl | 3-fluoropropyl | |
| 8.10 | H | ethyl | Z-3-chloroprop-2-enyl | |
| 8.11 | H | ethyl | 2-chloroprop-2-enyl | |
| 8.12 | H | ethyl | but-2-ynyl | |
| 8.13 | H | ethyl | 2-methoxyethyl | |
| 8.14 | H | ethyl | E-4(4-t-butylphenyl)but-2-enyl | |
| 8.15 | H | ethyl | E-4(4-fluorophenyl)but-2-enyl | |
| 8.16 | H | ethyl | E-4(4-chlorophenyl)but-2-enyl | |
| 8.17 | H | ethyl | E-4(4-trifluoromethyl-phenyl)but-2-enyl | |
| 8.18 | H | ethyl | E-4-phenylbut-2-enyl | |
| 8.19 | H | ethyl | benzyl | |
| 8.20 | H | ethyl | 4-fluorobenzyl | |
| 8.21 | H | ethyl | 3-trifluoromethylbenzyl | |
| 8.22 | H | ethyl | 4-nitrobenzyl | |
| 8.23 | H | ethyl | 4-cyanobenzyl | |
| 8.24 | H | ethyl | 3-chlorobenzyl | |
| 8.25 | H | ethyl | thien-2-ylmethyl | |
| 8.26 | H | ethyl | 5-bromothien-2-ylmethyl | |
| 8.27 | H | propyl | ethyl | |
| 8.28 | H | propyl | allyl | |
| 8.29 | H | propyl | E-3-chloroprop-2-enyl | |
| 8.30 | H | propyl | E-but-2-enyl | |
| 8.31 | H | propyl | 5-chlorothien-2-ylmethyl | |
| 8.32 | H | propyl | methyl | |
| 8.33 | H | propyl | propyl | |
| 8.34 | H | propyl | prop-2-ynyl | |
| 8.35 | H | propyl | 3-fluoropropyl | |
| 8.36 | H | propyl | Z-3-chloroprop-2-enyl | |
| 8.37 | H | propyl | 2-chloroprop-2-enyl | |
| 8.38 | H | propyl | but-2-ynyl | |
| 8.39 | H | propyl | 2-methoxyethyl | |
| 8.40 | H | propyl | E-4(4-butylphenyl)but-2-enyl | |
| 8.41 | H | propyl | E-4(4-fluorophenyl)but-2-enyl | |
| 8.42 | H | propyl | E-4(4-chlorophenyl)but-2-enyl | |
| 8.43 | H | propyl | E-4(4-trifluoromethyl-phenyl)but-2-enyl | |
| 8.44 | H | propyl | E-4-phenylbut-2-enyl | |
| 8.45 | H | propyl | benzyl | |
| 8.46 | H | propyl | 4-fluorobenzyl | |
| 8.47 | H | propyl | 3-trifluoromethylbenzyl | |
| 8.48 | H | propyl | 4-nitrobenzyl | |
| 8.49 | H | propyl | 4-cyanobenzyl | |
| 8.50 | H | propyl | 3-chlorobenzyl | |
| 8.51 | H | propyl | thien-2-ylmethyl | |
| 8.52 | H | propyl | 5-bromothien-2-ylmethyl | |

TABLE 9

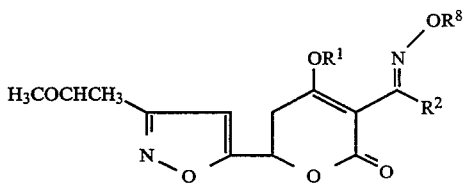

| No. | R¹ | R² | R⁸ | Phys. data mp [°C.]; NMR [δ, ppm] |
|---|---|---|---|---|
| 9.1 | H | ethyl | ethyl | |
| 9.2 | H | ethyl | allyl | |
| 9.3 | H | ethyl | E-3-chloroprop-2-enyl | |
| 9.4 | H | ethyl | E-but-2-enyl | |
| 9.5 | H | ethyl | 5-chlorothien-2-ylmethyl | |
| 9.6 | H | ethyl | methyl | |
| 9.7 | H | ethyl | propyl | |
| 9.8 | H | ethyl | prop-2-ynyl | |
| 9.9 | H | ethyl | 3-fluoropropyl | |
| 9.10 | H | ethyl | Z-3-chloroprop-2-enyl | |
| 9.11 | H | ethyl | 2-chloroprop-2-enyl | |
| 9.12 | H | ethyl | but-2-ynyl | |
| 9.13 | H | ethyl | 2-methoxyethyl | |
| 9.14 | H | ethyl | E-4(4-butylphenyl)but-2-enyl | |
| 9.15 | H | ethyl | E-4(4-fluorophenyl)but-2-enyl | |
| 9.16 | H | ethyl | E-4(4-chlorophenyl)but-2-enyl | |
| 9.17 | H | ethyl | E-4(4-trifluoromethylphenyl)but-2-enyl | |
| 9.18 | H | ethyl | E-4-phenylbut-2-enyl | |
| 9.19 | H | ethyl | benzyl | |
| 9.20 | H | ethyl | 4-fluorobenzyl | |
| 9.21 | H | ethyl | 3-trifluoromethylbenzyl | |
| 9.22 | H | ethyl | 4-nitrobenzyl | |
| 9.23 | H | ethyl | 4-cyanobenzyl | |
| 9.24 | H | ethyl | 3-chlorobenzyl | |
| 9.25 | H | ethyl | thien-2-ylmethyl | |
| 9.26 | H | ethyl | 5-bromothien-2-ylmethyl | |
| 9.27 | H | propyl | ethyl | |
| 9.28 | H | propyl | allyl | |
| 9.29 | H | propyl | E-3-chloroprop-2-enyl | |
| 9.30 | H | propyl | E-but-2-enyl | |
| 9.31 | H | propyl | 5-chlorothien-2-ylmethyl | |
| 9.32 | H | propyl | methyl | |
| 9.33 | H | propyl | propyl | |
| 9.34 | H | propyl | prop-2-ynyl | |
| 9.35 | H | propyl | 3-fluoropropyl | |
| 9.36 | H | propyl | Z-3-chloroprop-2-enyl | |
| 9.37 | H | propyl | 2-chloroprop-2-enyl | |
| 9.38 | H | propyl | but-2-ynyl | |
| 9.39 | H | propyl | 2-methoxyethyl | |
| 9.40 | H | propyl | E-4(4-t-butylphenyl)but-2-enyl | |
| 9.41 | H | propyl | E-4(4-fluorophenyl)but-2-enyl | |
| 9.42 | H | propyl | E-4(4-chlorophenyl)but-2-enyl | |
| 9.43 | H | propyl | E-4(4-trifluoromethylphenyl)but-2-enyl | |
| 9.44 | H | propyl | E-4-phenylbut-2-enyl | |
| 9.45 | H | propyl | benzyl | |
| 9.46 | H | propyl | 4-fluorobenzyl | |
| 9.47 | H | propyl | 3-trifluoromethylbenzyl | |
| 9.48 | H | propyl | 4-nitrobenzyl | |
| 9.49 | H | propyl | 4-cyanobenzyl | |
| 9.50 | H | propyl | 3-chlorobenzyl | |
| 9.51 | H | propyl | thien-2-ylmethyl | |
| 9.52 | H | propyl | 5-bromothien-2-ylmethyl | |

TABLE 10

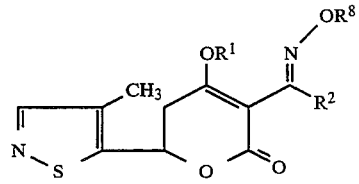

| No. | R¹ | R² | R⁸ | Phys. data mp [°C.]; NMR [δ, ppm] |
|---|---|---|---|---|
| 10.1 | H | ethyl | ethyl | |
| 10.2 | H | ethyl | allyl | |
| 10.3 | H | ethyl | E-3-chloroprop-2-enyl | |
| 10.4 | H | ethyl | E-but-2-enyl | |
| 10.5 | H | ethyl | 5-chlorothien-2-ylmethyl | |
| 10.6 | H | propyl | ethyl | 1.02(t, 3H); 1.39(t, 3H); 2.3(s, 3H); 4.14(q, 2H); 5.47(dd, 1H) |
| 10.7 | H | propyl | allyl | 1.02(t, 3H); 2.3(s, 3H); 4.56(d, 2H); 5.25–5.55 (m, 2H); 5.7(dd, 1H) |
| 10.8 | H | propyl | E-3-chloroprop-2-enyl | 1.0(t, 3H); 2.28(s, 3H); 4.55(d, 2H); 5.71(dd, 1H); 6.0–6.2(m, 1H) |
| 10.9 | H | propyl | E-but-2-enyl | 1.03(t, 3H); 1.82(d, 3H); 2.3(s, 3H); 4.47(d, 2H); 5.55–5.75(m, 2H) |
| 10.10 | H | propyl | 5-chlorothien-2-ylmethyl | |

TABLE 11

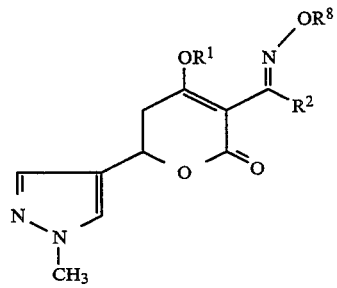

| No. | R¹ | R² | R⁸ | Phys. data mp [°C.]; NMR [δ, ppm] |
|---|---|---|---|---|
| 11.1 | H | ethyl | ethyl | |
| 11.2 | H | ethyl | allyl | 1.2(t, 3H); 3.9(s, 3H); 4.55(d, 2H); 5.2–5.6(m, 3H); 5.85–6.15(m, 1H) |
| 11.3 | H | ethyl | E-3-chloroprop-2-enyl | 1.16(t, 3H); 3.9(s, 3H); 4.55(d, 2H); 5.42 (dd, 1H); 6.0–6.2 (m, 1H) |
| 11.4 | H | ethyl | E-but-2-enyl | 1.2(t, 3H); 1.78(d, 3H); 3.9(s, 3H); 4.47 (d, 2H); 5.4(dd, 1H) |
| 11.5 | H | ethyl | 5-chlorothien-2-ylmethyl | 1.16(t, 3H); 3.9(s, 3H); 5.1(s, 2H); 5.4 (dd, 1H); 6.83(d, 1H) |
| 11.6 | H | propyl | ethyl | |
| 11.7 | H | propyl | allyl | |
| 11.8 | H | propyl | E-3-chloroprop-2-enyl | |
| 11.9 | H | propyl | E-but-2-enyl | |
| 11.10 | H | propyl | 5-chlorothien-2-ylmethyl | |
| 11.11 | H | ethyl | E-4-(4-fluorphenyl)-but-2-enyl | 1.19(t, 3H); 3.42(d, 2H); 3.88(s, 3H); 4.5 (d, 2H); 5.4(dd, 1H) |
| 11.12 | H | ethyl | 3-trifluoromethylphenyl | 1.18(t, 3H); 3.9(s, 3H); 5.14(s, 2H); 5.4 |

TABLE 11-continued

[Chemical structure: pyran-2-one with OR¹, =N-OR⁸, R² substituents and N-methylpyrazole group]

| No. | R¹ | R² | R⁸ | Phys. data mp [°C]; NMR [δ, ppm] |
|---|---|---|---|---|
| 11.13 | H | ethyl | but-2-ynyl | (dd, 1H); 7.4–7.7 (m, 6H) 1.19(t, 3H); 1.9(t, 3H); 3.91(s, 3H); 4.62(d, 2H); 5.44(dd, 1H) |
| 11.14 | H | ethyl | prop-2-ynyl | 0.86(t, 3H); 0.95(t, 3H); 1.26(d, 3H); 2.59(t, 1H); 4.67(d, 2H); 5.53(dd, 1H) |

TABLE 12

[Chemical structure with (H₃C)₂N-C(=N)-S- thiazoline-linked pyran-2-one]

| No. | R¹ | R² | R⁸ | Phys. data mp [°C]; NMR [δ, ppm] |
|---|---|---|---|---|
| 12.1 | H | ethyl | ethyl | |
| 12.2 | H | ethyl | allyl | |
| 12.3 | H | ethyl | E-3-chloroprop-2-enyl | |
| 12.4 | H | ethyl | E-but-2-enyl | |
| 12.5 | H | ethyl | 5-chlorothien-2-ylmethyl | |
| 12.6 | H | propyl | ethyl | |
| 12.7 | H | propyl | allyl | |
| 12.8 | H | propyl | E-3-chloroprop-2-enyl | |
| 12.9 | H | propyl | E-but-2-enyl | |
| 12.10 | H | propyl | 5-chlorothien-2-ylmethyl | |

TABLE 13

[Chemical structure: 4-fluorophenyl-thienyl linked pyran-2-one]

| No. | R¹ | R² | R⁸ | Phys. data mp [°C]; NMR [δ, ppm] |
|---|---|---|---|---|
| 13.1 | H | ethyl | ethyl | |
| 13.2 | H | ethyl | allyl | |
| 13.3 | H | ethyl | E-3-chloroprop-2-enyl | |
| 13.4 | H | ethyl | E-but-2-enyl | |
| 13.5 | H | ethyl | 5-chlorothien-2-ylmethyl | |
| 13.6 | H | propyl | ethyl | |
| 13.7 | H | propyl | allyl | |

TABLE 13-continued

[Chemical structure continued]

| No. | R¹ | R² | R⁸ | Phys. data mp [°C]; NMR [δ, ppm] |
|---|---|---|---|---|
| 13.8 | H | propyl | E-3-chloroprop-2-enyl | |
| 13.9 | H | propyl | E-but-2-enyl | |
| 13.10 | H | propyl | 5-chlorothien-2-ylmethyl | |

TABLE 14

[Chemical structure: N-benzyl pyrrole linked pyran-2-one]

| No. | R¹ | R² | R⁸ | Phys. data mp [°C]; NMR [δ, ppm] |
|---|---|---|---|---|
| 14.1 | H | ethyl | ethyl | |
| 14.2 | H | ethyl | allyl | |
| 14.3 | H | ethyl | E-3-chloroprop-2-enyl | |
| 14.4 | H | ethyl | E-but-2-enyl | |
| 14.5 | H | ethyl | 5-chlorothien-2-ylmethyl | |
| 14.6 | H | propyl | ethyl | |
| 14.7 | H | propyl | allyl | 0.98(t, 3H); 3.5(dd, 1H); 4.53 (dd, 2H); 5.1–5.5(m, 4H); 5.8–6.1(m, 1H) |
| 14.8 | H | propyl | E-3-chloroprop-2-enyl | 0.95(t, 3H); 1.55(dt, 2H); 4.52 (d, 2H); 6.0–6.2(m, 1H); 6.38(d, 1H) |
| 14.9 | H | propyl | E-but-2-enyl | 0.96(t, 3H); 1.79(d, 3H); 4.44 (d, 2H); 5.5–6.0(m, 2H); 6.85–7.4(m, 7H) |
| 14.10 | H | propyl | 5-chlorothien-2-ylmethyl | 0.94(t, 3H); 1.54(dt, 2H); 5.08(s, 2H); 6.6–7.4(m, 9H) |
| 14.11 | H | propyl | E-4-(4-fluorophenyl)-but-2-enyl | 0.98(t, 3H); 1.58(dt, 2H); 4.5 (d, 2H); 5.5–5.75(m, 1H); 5.9–6.1(m, 1H) |
| 14.12 | H | propyl | prop-2-ynyl | 0.94(s, 3H); 2.55(t, 1H); 4.67 (t, 2H); 5.1–5.35(m, 3H); 6.85–7.5(m, 7H) |

USE EXAMPLES

The herbicidal action of the tetrahydropyran-2,4-derivatives of the formula I where Z is an oxime ether group (—NOR⁸) is demonstrated by the following greenhouse experiments:

The vessels employed were plastic flowerpots having a volume of 300 cm³ and filled with a sandy loam containing about 3.0% humus. The seeds of the test plants were sown separately, according to species.

For the preemergence treatment, the active ingredients were applied to the surface of the soil immediately after the seeds had been sown. The compounds were emulsified or suspended in water as vehicle, and sprayed through finely distributing nozzles. The application rate was 0.5 kg of active ingredient per hectare. After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were grown, depending on growth form, to a height of 3 to 15 cm before being treated. In this treatment method, either plants which had been sown in the pots and grown there were selected, or they were cultivated separately as seedlings and transplanted to the pots a few days before being treated. The application rate for postemergence treatment was 0.5 kg/ha. No covers were placed on the vessels in this method.

The pots were set up in the greenhouse, species from warmer climates in warmer areas (20° to 35° C.) and species from moderate climates at 10° to 25° C. The experiments were run for from 2 to 4 weeks. During this time the plants were tended and their reactions to the various treatments assessed. The assessment scale was 0 to 100, 100 denoting nonemergence or complete destruction of at least the visible plant parts, and 0 denoting no damage or normal growth.

The plants used in the greenhouse experiments were Avena fatua, Alopecurus myosuroides, Echinochloa crus-galli, Setaria fatua, Setaria viridis, and Triticum aestivum.

Active ingredient 4.1 selected by way of example had, on postemergence application of 0.5 kg/ha, a herbicidal action on grassy plants and was tolerated by a crop plant. Compound 4.3, applied in the greenhouse at a rate of 0.25 kg/ha, controlled unwanted grasses.

Compounds I in which Z is an oxime ether group ($-NOR^8$) are tolerated by, and are therefore selective in, broadleaved crops and in monocotyledonous plants not belonging to the Gramineae. Furthermore, they are suitable for combating unwanted grasses in graminaceous crops such as wheat and rice.

We claim:

1. Tetrahydropyran-2,4-diones of the formulae I.1, I.3, I.4 and I.6 to I.39

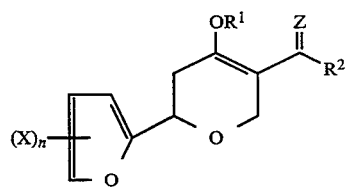

I.1

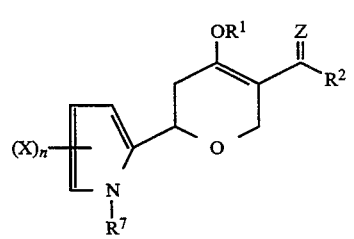

I.3

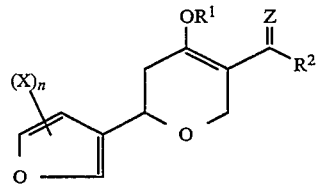

I.4

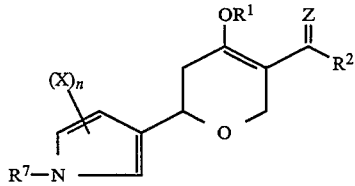

I.6

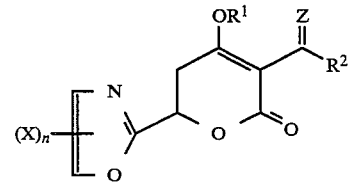

I.7

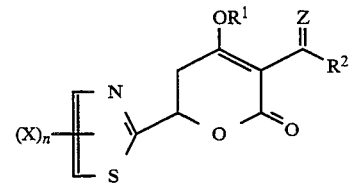

I.8

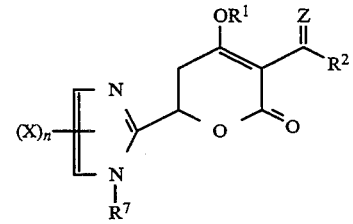

I.9

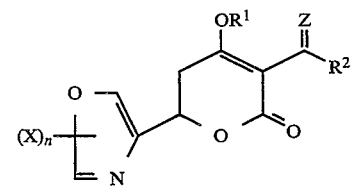

I.10

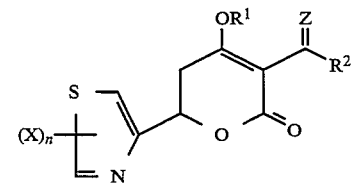

I.11

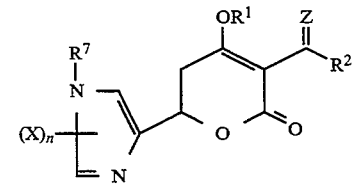

I.12

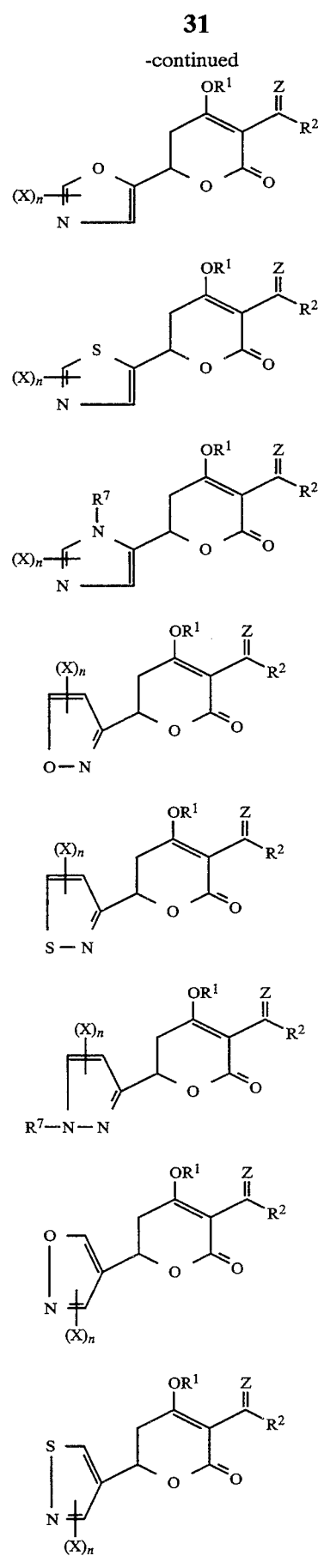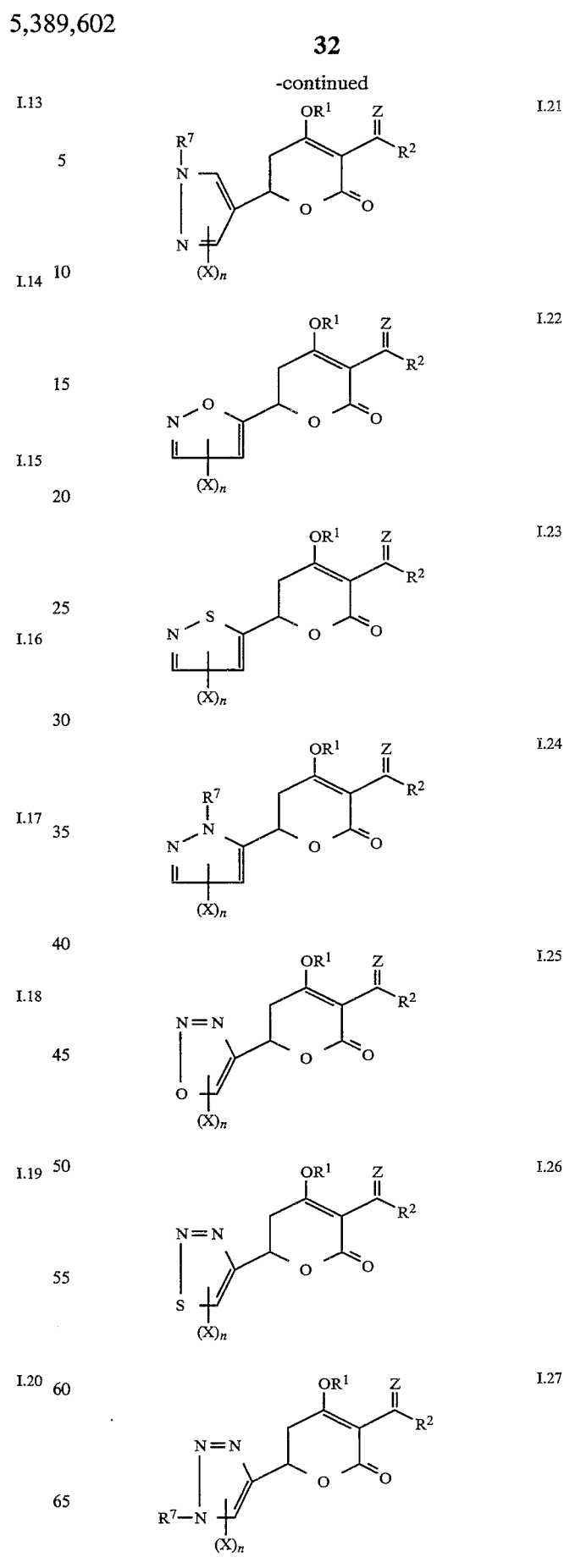

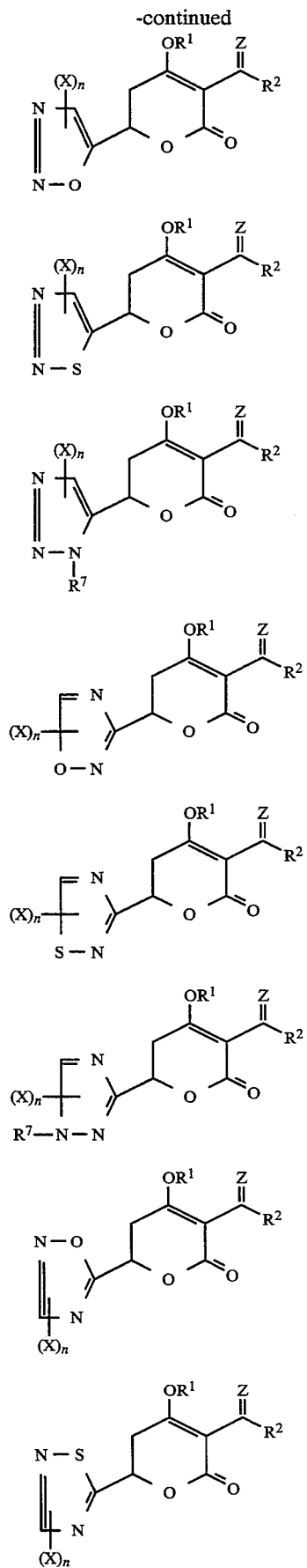

where
R¹ is hydrogen; $C_1$-$C_8$-alkyl which may be substituted by $C_1$-$C_6$-alkoxy or $C_1$-$C_6$-alkylthio; $C_2$-$C_6$-alkenyl; $C_2$-$C_6$-alkynyl; phenyl which may be monosubstituted to trisubstituted by halogen, nitro, cyano, $C_1$-$C_6$-alkyl, $C_1$-$C_6$-haloalkyl; $C_1$-$C_6$-alkoxy and/or $C_1$-$C_6$-alkylthio; $C_1$-$C_6$-alkylsulfonyl; benzenesulfonyl which may be monosubstituted to trisubstituted in the benzene ring by halogen, nitro, cyano, $C_1$-$C_6$-alkyl, $C_1$-$C_6$-haloalkyl, $C_1$-$C_6$-alkoxy and/or $C_1$-$C_6$-alkylthio; $C_2$-$C_6$-alkylcarbonyl; $C_3$-$C_6$-alkenylcarbonyl; or benzoyl which may be monosubstituted to trisubstituted in the benzene ring by halogen, cyano, nitro, $C_1$-$C_6$-alkyl, $C_1$-$C_6$-haloalkyl, $C_1$-$C_6$-alkoxy or $C_1$-$C_6$-alkylthio;

R² is $C_1$-$C_6$-alkyl, $C_2$-$C_6$-alkenyl, $C_2$-$C_6$-alkynyl, $C_1$-$C_6$-haloalkyl or $C_3$-$C_6$-cycloalkyl;

R⁷ is hydrogen; $C_1$-$C_6$-alkyl; $C_2$-$C_6$-alkenyl; $C_2$-$C_6$-alkanoyl; benzoyl which may be monosubstituted to trisubstituted in the benzene ring by $C_1$-$C_6$-alkyl, $C_1$-$C_6$-alkoxy, $C_1$-$C_6$-alkylthio, halogen, cyano, nitro and/or $C_1$-$C_6$-haloalkyl; benzyl; or phenyl which may be monosubstituted to trisubstituted by halogen, nitro, cyano, $C_1$-$C_6$-alkyl, $C_1$-$C_6$-haloalkyl, $C_1$-$C_6$-alkoxy and/or $C_1$-$C_6$-alkylthio; X is halogen; $C_1$-$C_6$-alkyl; $C_3$-$C_6$-cycloalkyl which may be monosubstituted to trisubstituted by halogen, $C_1$-$C_6$-alkoxy and/or $C_1$-$C_6$-alkylthio; $C_2$-$C_6$-alkenyl; $C_2$-$C_6$-alkynyl; $C_1$-$C_6$-alkoxy; $C_2$-$C_6$-alkenyloxy; $C_1$-$C_6$-alkylthio; $C_1$-$C_6$-alkoxycarbonyl; $C_2$-$C_6$-alkanoyloxy; benzyloxy which may be monosubstituted to trisubstituted in the benzene ring by halogen, nitro, cyano, $C_1$-$C_6$-alkyl, $C_1$-$C_6$-alkoxy and/or $C_1$-$C_6$-haloalkyl; $NR^5R^6$; formyl or $C_2$-$C_6$-alkanoyl or its imine, oxime or Schiff's base; or phenyl which may be monosubstituted to trisubstituted by halogen, nitro, cyano, $C_1$-$C_6$-alkyl, $C_1$-$C_6$-alkoxy, $C_1$-$C_6$-haloalkyl and/or $NR^3R^4$;

n is 0, 1 or 2 and, where n is 2, the radicals X may be different;

$R^3$, $R^4$, $R^5$ and $R^6$ are each hydrogen, $C_1$-$C_6$-alkyl, phenyl, $C_2$-$C_6$-alkanoyl, benzoyl and/or benzyl;

Z is oxygen or an oxime ether radical —$NOR^8$; and $R^8$ is $C_1$-$C_6$-alkyl or $C_2$-$C_6$-alkenyl which may be monosubstituted to trisubstituted by halogen, $C_1$-$C_6$-alkoxy and/or $C_1$-$C_6$-alkylthio; $C_2$-$C_6$-alkynyl; $C_2$-$C_6$-haloalkynyl; $C_1$-$C_6$-alkyl or $C_2$-$C_6$-alkenyl, each of which may be monosubstituted to trisubstituted by phenyl, which may be monosubstituted to trisubstituted by halogen, nitro, cyano, $C_1$-$C_6$-alkyl, $C_1$-$C_6$-haloalkyl, $C_1$-$C_6$-alkoxy and/or $C_1$-$C_6$-alkylthio; or thenyl which may be monosubstituted to trisubstituted by halogen, or their environmentally compatible salts.

2. Tetrahydropyrandiones of the formula Ia

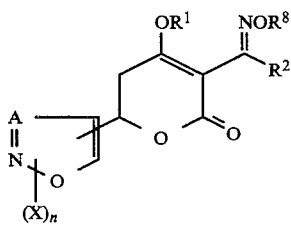

wherein $R^1$ is hydrogen; $C_1$-$C_6$-alkyl which may be substituted by $C_1$-$C_6$-alkoxy or $C_1$-$C_6$-alkylthio; $C_2$-$C_6$-alkenyl; $C_2$-$C_6$-alkynyl; phenyl which may monosubstituted to trisubstituted by halogen, nitro, cyano, $C_1$-$C_6$-alkyl, $C_1$-$C_6$-haloalkyl, $C_1$-$C_6$-alkoxy and/or $C_1$-$C_6$-alkylthio; $C_1$-$C_6$-alkylsulfonyl; benzenesulfonyl which may be mono-substituted to trisubstituted in the benzene ring by halogen, nitro, cyano, $C_1$-$C_6$-alkyl, $C_1$-$C_6$-haloalkyl, $C_1$-$C_6$-alkoxy and/or $C_1$-$C_6$-alkylthio; $C_2$-$C_6$-alkylcarbonyl; $C_3$-$C_6$-alkenylcarbonyl; or benzoyl which may be monosubstituted to trisubstituted in the benzene ring by halogen, cyano, nitro, $C_1$-$C_6$-alkyl, $C_1$-$C_6$-haloalkyl, $C_1$-$C_6$-alkoxy or $C_1$-$C_6$-alkylthio;

$R^2$ is $C_1$-$C_6$-alkyl; $C_2$-$C_6$-alkenyl; $C_2$-$C_6$-alkynyl; $C_1$-$C_6$-haloalkyl; or $C_3$-$C_6$-cycloalkyl;

A is =CH— or =N—;

X is halogen; $C_1$-$C_6$-alkyl; $C_3$-$C_6$-cycloalkyl which may be mono-substituted to trisubstituted by halogen, $C_1$-$C_6$-alkoxy and/or $C_1$-$C_6$-alkylthio; $C_2$-$C_6$-alkenyl; $C_2$-$C_6$-alkynyl; $C_1$-$C_6$-alkoxy; $C_2$-$C_6$-alkenyloxy; $C_1$-$C_6$-alkylthio; $C_1$-$C_6$-alkoxycarbonyl; $C_2$-$C_6$-alkanoyloxy; benzyloxy which may be monosubstituted to trisubstituted in the benzene ring by halogen, nitro, cyano, $C_1$-$C_6$-alkyl, $C_1$-$C_6$-alkoxy and/or $C1$-$C_6$-haloalkyl; $NR^5R^6$; formyl or $C_2$-$C_6$-alkanoyl or its imine, oxime or Schiff's base; or phenyl which may be monosubstituted to trisubstituted by halogen, nitro, cyano, $C_1$-$C_6$-alkyl, $C_1$-$C_6$-alkoxy, $C_1$-$C_6$-haloalkyl and/or $NR^3R^4$;

n is 0, 1 or 2, and, where n is 2, the radicals may be different;

$R^3$, $R^4$, $R^5$ and $R^6$ are each hydrogen, $C_1$-$C_6$-alkyl, phenyl, $C_2$-$C_6$ alkanoyl, benzoyl and/or benzyl; and $R^8$ is $C_1$-$C_6$-alkyl or $C_2$-$C_6$-alkenyl which may be monosubstituted to trisubstituted by halogen, $C_1$-$C_6$-alkoxy and/or $C_1$-$C_6$-alkylthio; $C_2$-$C_6$-alkynyl; $C_2$-$C_6$-haloalkynyl; $C_1$-$C_6$-alkyl or $C_2$-$C_6$-alkenyl, each of which may be monosubstituted to trisubstituted by phenyl, which may be monosubstituted to trisubstituted by halogen, nitro, cyano, $C_1$-$C_6$-alkyl, $C_1$-$C_6$-haloalkyl, $C_1$-$C_6$-alkoxy and/or $C_1$-$C_6$-alkylthio; or thenyl which may be monosubstituted or trisubstituted by halogen, and their environmentally compatible salts.

3. The compound of claim 1 which

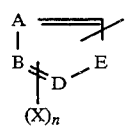

is selected from the group consisting of isoxazole, furan and pyrazole compounds.

4. The compound of claim 2 wherein

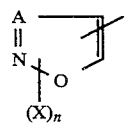

is isoxazole.

5. The compound of claim 3 wherein X is $C_1$-$C_6$ alkyl and n is 1.

6. The compound of claim 4 wherein X is $C_1$-$C_6$ alkyl and n is 1.

7. Tetrahydropyran-2,4-diones of the formula I as set forth in claim 1, wherein E is oxygen or —$NR^7$—.

8. A herbicidal agent containing a tetrahydropyran-2,4-dione of the formula I as set forth in claim 1, Z denoting the radical —$NOR^8$.

9. A plant growth-regulating agent containing a tetrahydropyran-2,4-dione of the formula I as set forth in claim 1, Z denoting oxygen.

10. A process for combating the growth of unwanted plants, wherein the unwanted plants and/or the area to be kept free from unwanted plant growth are treated with a herbicidally effective amount of a tetrahydropyran-2,4-dione of the formula I as set forth in claim 1, Z denoting —$NOR^8$.

11. A process for regulating plant growth, wherein an amount effective for growth regulation of a tetrahydropyran-2,4-dione of the formula I as set forth in claim 1, Z denoting oxygen, is allowed to act on seeds, plants and/or their habitat.

* * * * *